United States Patent
Reeve (10) Patent No.: US 7,606,622 B2
(45) Date of Patent: Oct. 20, 2009

(54) METHOD AND DEVICE FOR DETECTING AND TREATING DEPRESSION

(75) Inventor: Helen L. Reeve, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 514 days.

(21) Appl. No.: 11/275,682

(22) Filed: Jan. 24, 2006

(65) Prior Publication Data

US 2007/0173901 A1  Jul. 26, 2007

(51) Int. Cl.
*A61N 1/08* (2006.01)
(52) U.S. Cl. .................... 607/45; 607/3; 607/62
(58) Field of Classification Search ........... 600/509; 607/2, 9, 33, 45, 115, 116; D/509
See application file for complete search history.

(56) References Cited

U.S. PATENT DOCUMENTS

| | | | |
|---|---|---|---|
| 5,299,569 A * | 4/1994 | Wernicke et al. | 607/45 |
| 6,141,588 A * | 10/2000 | Cox et al. | 607/9 |
| 6,176,242 B1 * | 1/2001 | Rise | 128/898 |
| 6,356,784 B1 * | 3/2002 | Lozano et al. | 607/2 |
| 6,361,522 B1 | 3/2002 | Scheiner et al. | |
| 2002/0193838 A1 | 12/2002 | Lovett | |
| 2003/0023282 A1* | 1/2003 | Barrett et al. | 607/45 |
| 2004/0249429 A1* | 12/2004 | Tadlock | 607/116 |
| 2004/0267142 A1* | 12/2004 | Paul | 600/509 |
| 2005/0015129 A1* | 1/2005 | Mische | 607/115 |
| 2005/0033379 A1 | 2/2005 | Lozano et al. | |
| 2005/0043774 A1* | 2/2005 | Devlin et al. | 607/45 |
| 2005/0049651 A1 | 3/2005 | Whitehurst et al. | |
| 2005/0049655 A1 | 3/2005 | Boveja et al. | |
| 2005/0113744 A1 | 5/2005 | Donoghue et al. | |
| 2007/0203531 A9* | 8/2007 | Starkebaum | 607/40 |

FOREIGN PATENT DOCUMENTS

| | | |
|---|---|---|
| WO | WO-93/02744 A1 | 2/1993 |
| WO | WO 2007/087192 * | 8/2007 |
| WO | WO-2007/087192 A2 | 8/2007 |

OTHER PUBLICATIONS

PCT Application No. PCT/US2007/001086, International Search Report mailed Jul. 19, 2007, 5 pgs.
PCT Application No. PCT/US2007/001086, Written Opinion mailed Jul. 19, 2007, 7 pgs.
Carney, R. M., et al., "Association of Depression With Reduced Heart Rate Variability in Coronary Artery Disease.", *The American Journal of Cardiology*, 76(8), (1995), 562-564.
De Denus, S., et al., "History of Depression as a Predictor of Adverse Outcomes in Patients Hospitalized for Decompensated Heart Failure.", *Pharmacotherapy*, 24(10), (2004), 1306-1310.
Hughes, J. W., et al., "Depression and Anxiety Symptoms are Related to Increased 24-Hour Urinary Norepinephrine Excretion Among Healthy Middle-Aged Women.", *Journal of Psychosomatic Research*, 57(4), (2004), 353-358.

(Continued)

*Primary Examiner*—Carl H Layno
*Assistant Examiner*—Luther G Behringer
(74) *Attorney, Agent, or Firm*—Schwegman, Lundberg & Woessner, P.A.

(57) ABSTRACT

A system is described for detecting and/or treating depression that may be incorporated into an implantable device such as a cardiac rhythm management device. The device may determine that depression is present by analysis of heart rate variability measured using the cardiac sensing channels of the device and/or by detection of blood-borne factors that are associated with depression. If depression is detected, the device may be configured to automatically delivery therapy such as neuromodulation and/or drug delivery.

16 Claims, 4 Drawing Sheets

OTHER PUBLICATIONS

Irani, S. R., "A Novel Neurological Mechanism to Explain the Adverse Effect of Depression on Coronary Artery Disease.", *Medical Hypotheses*, 64(2), (2005), 284-287.

Januzzi, Jr., J. L., et al., "The Influence of Anxiety and Depression on Outcomes of Patients With Coronary Artery Disease", *Archives of Internal Medicine*, 160(13), (2000), 1913-1921.

Jünger, J., et al., "Depression Increasingly Predicts Mortality in the Course of Congestive Heart Failure.", *European Journal of Heart Failure*, 7(2), (2005), 261-267.

Kawachi, I., et al., "Prospective Study of Phobic Anxiety and Risk of Coronary Heart Disease in Men.", *Circulation*, 89(5), (1994), 1992-1997.

Kawachi, I., et al., "Symptoms of Anxiety and Risk of Coronary Heart Disease. The Normative Aging Study.", *Circulation*, 90(5), (1994), 2225-2229.

Ladron De Guevara, M. S., et al., "Worsening of Depressive Symptoms 6 Months After an Acute Coronary Event in Older Adults is Associated With Impairment of Cardiac Autonomic Function", *Journal of Affective Disorders*, 80, (2004), 257-262.

Mallik, S., et al., "Patients With Depressive Symptoms Have Lower Health Status Benefits After Coronary Artery Bypass Surgery.", *Circulation*, 111(3), (2005), 271-277.

Rumsfeld, J. S., et al., "Depression and Cardiovascular Disease: A Call For Recognition", *Circulation*, 111(3), (2000), 250-253.

Schins, A., et al., "Whole Blood Serotonin and Platelet Activation in Depressed Post-Myocardial Infarction Patients.", *Life Sciences*, 76(6), (2004), 637-650.

Sears Jr., S. F., et al., "Quality of Life and Psychological Functioning of ICD Patients.", *Heart*, 87(5), (2002), 488-493.

Serebruany, V. L., "Enhanced Platelet/Endothelial Activation in Depressed Patients With Acute Coronary Syndromes: Evidence From Recent Clinical Trials.", *Blood Coagulation & Fibrinolysis*, 14(6), (2003), 563-567.

Serebruany, V. L., et al., "Platelet/Endothelial Biomarkers in Depressed Patients Treated With the Selective Serotonin Reuptake Inhibitor Sertraline After Acute Coronary Events: the Sertraline AntiDepressant Heart Attack Randomized Trial (SADHART) Platelet Substudy", *Circulation*, 108(8), (2003), 939-944.

Vigo, D. E., et al., "Relation of Depression to Heart Rate Nonlinear Dynamics in Patients $\geq$ 60 Years of Age With Recent Unstable Angina Pectoris or Acute Myocardial Infarction.", *The American Journal of Cardiology*, 93(6), (2004), 756-760.

* cited by examiner

METHOD AND DEVICE FOR DETECTING AND TREATING DEPRESSION

FIELD OF THE INVENTION

This invention pertains to methods and systems for treating disease with implantable devices.

BACKGROUND

An epidemiologic link between depression and cardiovascular disease is well documented. Depression can be both a causative factor in the development of cardiovascular disease as well as a result of its development. Ironically, the development of cardiovascular disease is often likely to result in additional depressive symptoms in patients as the level of worry about their health increases, thus creating a vicious circle. Psychiatric disturbances such as severe depression have been reported in many patients receiving implantable cardioverter/defibrillators (ICDs). Approximately 65% of post-MI patients and up to 87% of ICD recipients reportedly have symptoms of mild or severe depression. Depression in patients with heart disease also has a clear effect on patient prognosis. It is well documented that heart failure patients, post-CABG patients and post-MI patients have a worsened prognosis if they have concomitant depression, including an increased risk for subsequent cardiac events such as re-hospitalizations and re-infarction. The worsening prognosis associated with depression is also consistent in other types of cardiovascular disease including unstable angina, CAD and heart failure. Post-CABG patients have been shown to not only have an increased risk of mortality, readmissions and cardiac events, but also to have a reduction in functional improvement post surgery. Clearly, breaking the vicious circle of cardiovascular disease and depression could have a significant impact on slowing the progression and clinical outcome of cardiovascular diseases in a significant number of patients. Depression has also been shown to be an important causative factor in many other diseases. A device based system for detection, signaling and potential treatment of depression, could significantly improve morbidity and mortality in these patients.

SUMMARY

This disclosure deals with a system for detecting and/or treating depression that may be incorporated into an implantable device such as a cardiac rhythm management device. The device may determine that depression is present by analysis of data acquired from its sensing channels relating to, for example, neural activity, heart rate variability measured using the cardiac sensing channels of the device, and/or by detection of blood-borne factors that are associated with depression. If depression is detected, the device may be configured to automatically delivery therapy such as neuromodulation and/or drug delivery. The device may also be interfaced to a patient management network via wireless telemetry and serve as a signaling system to alert medical personnel if depression is detected so that appropriate intervention may be initiated.

DETAILED DESCRIPTION

A system for detecting depression as described herein may be incorporated into an implantable device dedicated to that purpose or into a device with other functionality such a cardiac rhythm management device (i.e., a pacemaker or ICD). The device may be configured to only detect depression or may also be configured to automatically deliver one or more modes of anti-depressive therapy upon detection of depression. An implantable device configured to detect depression may also be equipped with a wireless telemetry system that is interfaced to a patient management network. Upon detecting an indication of depression, the device may be programmed to transmit a message over the network in order to alert clinical personnel.

The exact mechanism by which depression causes and worsens cardiovascular disease and patient prognosis is unknown, but it appears to be linked to modification of the autonomic nervous system activity. For example, urinary norepinephrine levels have been shown to be elevated in patients with depression and anxiety, such levels being due to increased activation of the sympathetic nervous system. Other markers of enhanced sympathetic activity related to heart rate are also found in depression, including decreased heart rate variability and increased heart rate. In various embodiments, the system may detect depression by direct measurement of neural activity at specific sites, measurement and analysis of heart rate, and/or by chemo-sensor detection of blood-borne markers shown to be specifically elevated in patients with depression. The system may also be configured to directly detect neural activity at peripheral or central sites that are found to be related to a patient's depressive episodes.

One way in which an implantable device may deliver anti-depressive therapy is by electrical stimulation to increase parasympathetic activity and/or inhibit sympathetic activity or electrical stimulation of sites within the brain, referred to herein as neuromodulation. For example, the vagus nerve may be electrically stimulated with an implanted electrode in order to increase parasympathetic activity. The device may also be configured to deliver deep brain electrical stimulation via an implanted stimulator or electrodes placed on the skull. The device may also be equipped with drug delivery capability in order to deliver anti-depressive drugs such as selective serotonin reuptake inhibitors (SSRIs), tricyclics antidepressants, monamine oxidase inhibitors (MAOIs), and serotonin and noradrenaline reuptake inhibitors (SNRIs).

Exemplary Implantable Device

Figure 1:
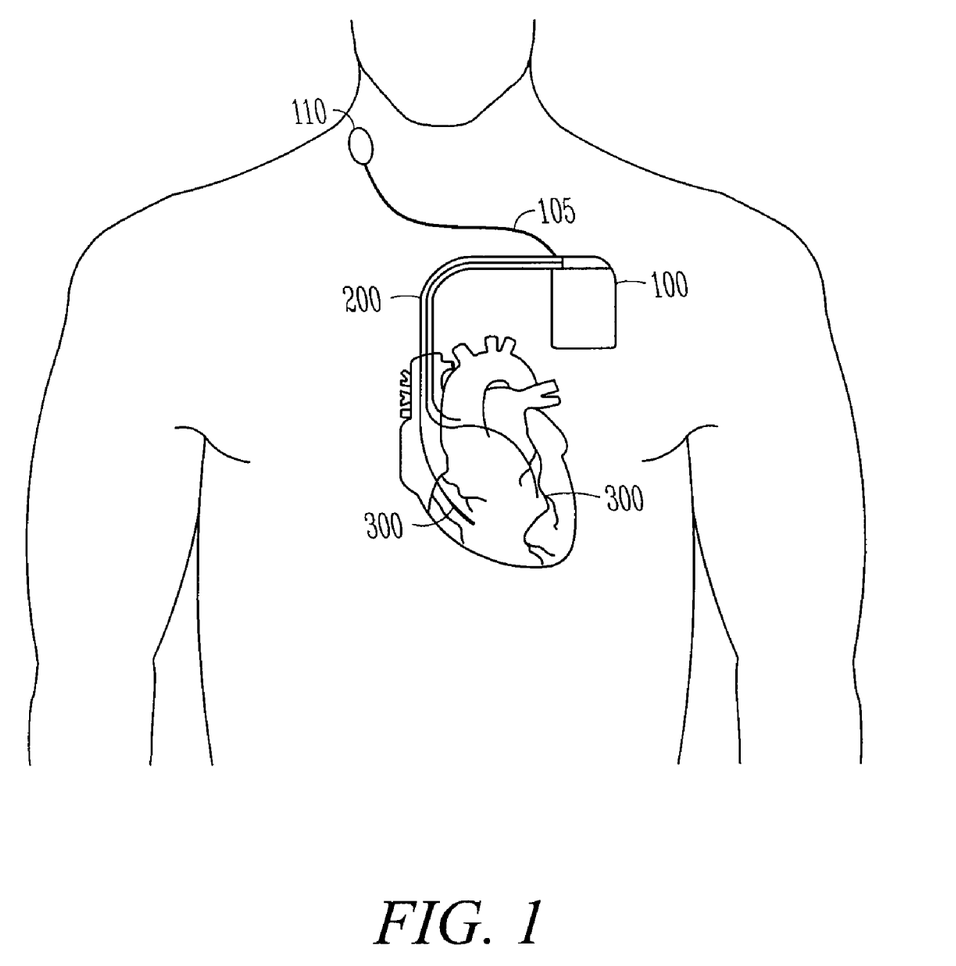
FIG. 1 illustrates the physical placement of an implantable cardiac device.

FIG. 1 shows an implantable device that may also be configured to detect and/or treat depression as described herein. The device housing 100 is placed subcutaneously or submuscularly in a patient's chest or other convenient location. Circuitry within the device housing includes a power supply, sensing circuitry, therapy circuitry, and a programmable electronic controller that interprets signal received from one or more sensing channels in order to detect depression, which, as the term is used herein, means detecting conditions that indicate there is a high probability that the patient is experiencing a depressive episode. The device controller may also cause the delivery of therapy, in the form of electrical stimulation and/or drug therapy, when depression is detected. In the embodiment depicted in FIG. 1, an electrode 110 is connected with the device circuitry via a lead 105 which passes subcutaneously from the device housing 100 to a point of venous access in the upper chest or neck. The electrode 110 is provided for neural stimulation and/or sensing and may be a direct nerve cuff or a transvascular lead placed in, for example, the internal jugular vein for transvascular stimulation or sensing of the vagus nerve. In one particular embodiment, an implantable device for treating and/or detecting depression may also be a cardiac rhythm management device. Such an embodiment is shown in FIG. 1 where the device also has one or more leads 200 threaded intravenously into the heart to connect the device to electrodes 300 used for sensing and pacing of the atria and/or ventricles. Electrodes may also be positioned on the epicardium by various means. The device controller causes electrical stimulation for pacing and/or terminating a tachyarrhythmia to be output in response to sensed cardiac electrical activity.

Figure 2:
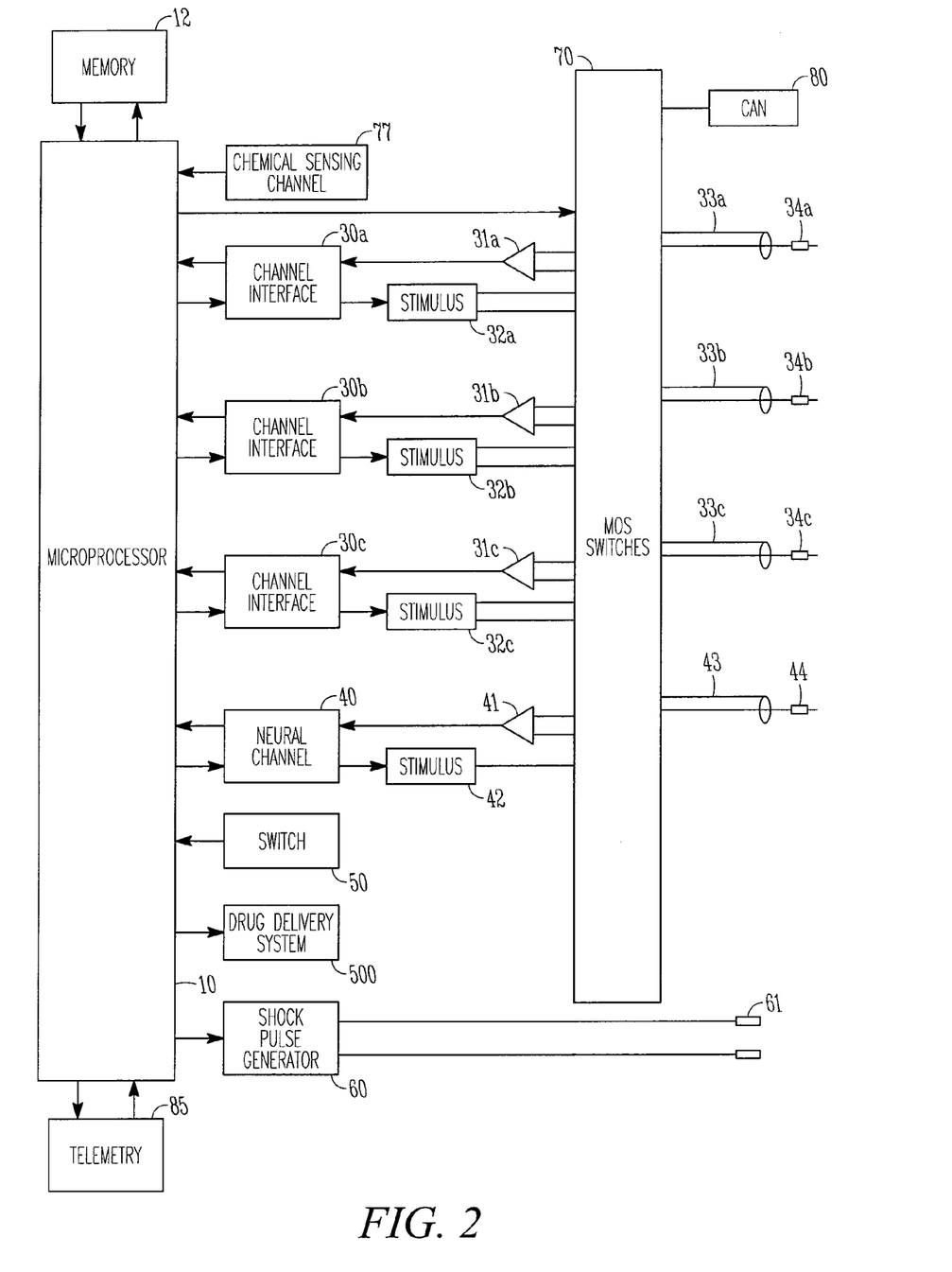
FIG. 2 is a block diagram of a cardiac rhythm management device with neuro-modulation and drug delivery capability.

FIG. 2 is a system diagram of a microprocessor-based cardiac rhythm management device with the capability of delivering cardioversion/defibrillation shocks, pacing therapy to the ventricles or the atria, drug delivery, and neural stimulation and that may be programmed to detect and/or treat depression. The controller of the device is a microprocessor 10 which communicates with a memory 12 via a bidirectional data bus. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor. Shown in the figure are three exemplary sensing and pacing channels designated "a" through "c" comprising bipolar leads with ring electrodes 33a-c and tip electrodes 34a-c, sensing amplifiers 31a-c, pulse generators 32a-c, and channel interfaces 30a-c. Each channel thus includes a pacing channel made up of the pulse generator connected to the electrode and a sensing channel made up of the sense amplifier connected to the electrode. The channel interfaces 30a-c communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect arrhythmias as well computing heart rate variability as described below.

The electrodes of each bipolar lead are connected via conductors within the lead to a MOS switching network 70 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 80 or an electrode on another lead serving as a ground electrode. A shock pulse generator 60 is also interfaced to the controller for delivering a defibrillation shock via a pair of shock electrodes 61 to the atria or ventricles upon detection of a shockable tachyarrhythmia.

One or more neural channels are incorporated into the device for delivering neural stimulation and/or sensing. Shown in FIG. 2 is a neural channel that includes a bipolar lead with a ring electrode 43 and a tip electrode 44, a pulse generator 42, sensing amplifier 41 and a channel interface 40. Other embodiments may use unipolar leads in which case the neural stimulation pulses or sensing signals are referenced to the can or another electrode. The pulse generator for a neural stimulation channel outputs a train of neural stimulation pulses, where the pulses may be varied by the controller as to amplitude, frequency, and duty-cycle. In one embodiment, the neural channel(s) uses a lead which can be intravascularly disposed near an appropriate site, e.g., near a baroreceptor in the case of a sympathetic inhibition channel or near a parasympathetic nerve in the case of a parasympathetic stimulation channel. Other types of leads and/or electrodes may also be employed. A nerve cuff electrode may be used in place of an intravascularly disposed electrode to provide neural stimulation, where the electrode may be placed, for example, around the cervical vagus nerve bundle to provide parasympathetic stimulation or around the aortic or carotid sinus nerve to provide sympathetic inhibition, as well as sensing of neural activity at those sites. In another embodiment, the leads of the neural stimulation electrodes are replaced by wireless links, and the electrodes for providing parasympathetic stimulation and/or sympathetic inhibition are incorporated into satellite units.

A magnetically or tactilely actuated switch 50 may be incorporated into the implantable device such as shown in FIG. 1. The switch may be used, for example, for initiating (or stopping) delivery of neural stimulation. The switch 50 may also be operated by the patient upon onset of depressive symptoms and thereby provide a history of when the patient is subjectively experiencing depression. As described below, such a history may be used by the device otherwise to optimize the detection of depression with sensed physiological parameters.

A telemetry transceiver 85 is provided for communicating with an external device such as an external programmer. An external programmer is a computerized device with an associated display and input means that can interrogate the implantable device and receive stored data as well as directly adjust operating parameters. The telemetry transceiver 85 enables the controller to communicate with an external device via a wireless telemetry link. The external device may be an external programmer which can be used to program the implantable device as well as receive data from it or may be a remote monitoring unit. The external device may also be interfaced to a patient management network enabling the implantable device to transmit data and alarm messages to clinical personnel over the network as well as be programmed remotely. Alarm messages may be transmitted, for example, when the device detects depression by the techniques described herein. Such alarm messages may allow clinical personnel to the track the progress of a patient's condition as well as intervene in certain situations. The network connection between the external device and the patient management network may be implemented by, for example, an internet connection, over a phone line, or via a cellular wireless link.

Detection of Depression

The device also is equipped with one or more chemical sensing channels 77 that provide the controller an indication of the concentration of a particular marker in the patient's blood. A chemical sensing channel includes a chemo-sensor designed to generate a voltage proportional to the concentration of a particular chemical species. The electrode is connected to the device by intravascular leads and disposed in the patient's blood in order to detect the concentration of one or more particular markers that have shown to be elevated in the presence of depression. Such markers may include, for example, serotonin, norepinephrine, platelet factor 4, beta-thromboglobulin, platelet/endothelial cell adhesion molecule-1, interleukin 6 (IL-6), tumor necrosis factor (TNF-$\alpha$), and C-reactive protein (CRP). Such chemo-sensors may use immobilized antibodies with binding affinities specific for the different marker antigens. Upon formation of an Ab-Ag complex between the antibody and the marker, the chemo-sensor may produce an electrical signal by, for example, incorporating a piezoelectric transducer that responds to mechanical stresses induced by the Ab-Ag complex (See, e.g., Biosens Bioelectron. 2005 Apr. 15; 20(10):1932-8, incorporated by reference) or a transducer that responds to potential changes resulting from the Ab-Ag complex. (See, e.g., Biosens Bioelectron. 2003 Oct. 1; 18(11):1385-90, incorporated by reference).

Another means for assessing whether depression is present is by determining the autonomic balance of the patient. It is well-known that an increase in the activity of the sympathetic nervous system may be indicative of depression. One means by which increased sympathetic activity may be detected is via spectral analysis of heart rate variability. Heart rate variability refers to the variability of the time intervals between successive heart beats during a sinus rhythm and is primarily due to the interaction between the sympathetic and parasympathetic arms of the autonomic nervous system. Spectral analysis of heart rate variability involves decomposing a signal representing successive beat-to-beat intervals into separate components representing the amplitude of the signal at different oscillation frequencies. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity. An LF/HF ratio which exceeds a specified threshold value may be taken as an indicator that cardiac function is not adequate. The device can be programmed to determine the LF/HF ratio by analyzing data received from its atrial or ventricular sensing channels. The intervals between successive atrial or ventricular senses, referred to as beat-to-beat or BB intervals, can be measured and collected for a period of time or a specified number of beats. The resulting series of RR interval values is then stored as a discrete signal and analyzed to determine its energies in the high and low frequency bands as described above. Techniques for estimating the LF/HF ratio based upon interval data are described in commonly assigned U.S. patent application Ser. No. 10/436,876 filed May 12, 2003, and Ser. No. 10/669,170 filed Sep. 23, 2003, the disclosures of which are hereby incorporated by reference. In one embodiment, the device stores the collected intervals as a discrete BB interval signal, filters the BB interval signal into defined high and low frequency bands, and determines the signal power of the BB interval signal in each of the low and high frequency bands, referred to LF and HF, respectively. The device then computes an LF/HF ratio and assesses autonomic balance by comparing the LF/HF ratio to a specified threshold value.

The device may also utilize one or more neural channels to detect increased or decreased neural activity at peripheral sites of autonomic nerves or within the brain. As described below with respect to neural stimulation, satellite units may be implanted within the brain having electrodes for sensing and/or stimulation that communicate wirelessly with the device controller.

The device may thus collect values of a number of different parameters found to be correlated with depression such as neural activity at one or more sites, blood concentration of different chemical markers, and cardiovascular parameters related to autonomic activity. Any, all, or some of these parameters may be used by the device to detect depression. For example, a measured parameter value (e.g., LF/HF ratio, marker concentration) may be compared with a specified threshold value. If the measured parameter value is greater than (or less than, depending upon the parameter) the specified threshold, depression is detected. In order to evaluate multiple depression parameter values in one embodiment, a plurality of such parameters are mapped into a depression index.

In one embodiment, the depression index is a numerically-valued function of the plurality of depression parameters that can be compared to a threshold value to determine if depression is deemed to be present. An example of such a depression index is a multi-linear function that is a weighted sum or average of a number of different parameters associated with depression:

$$DI = \Sigma w_i P_i \text{ for } i=1 \text{ through } N$$

where DI is the depression index, N is the number of depression parameters, $P_i$ is the $i^{-th}$ depression parameter, and $w_i$ is the weighting coefficient associated with $P_i$. The depression parameters may be measured values (e.g., LF/HF ratio, heart rate, blood pressure, blood protein marker level) or an integer value representing the presence or absence of a particular event or condition (e.g., a measurable parameter value above or below a specified threshold). The weighting coefficients may be positive in the case of a parameter that is positively correlated with depression or negative in the case of a parameter that is negatively correlated with depression. The optimal weighting coefficients for predicting depression with a particular sensitivity and/or specificity will generally vary from patient to patient. Optimal weighting coefficients may be determined for an individual patient from a history of how the parameters vary in relation to episodes of depression as subjectively reported by the patient and/or by clinical evaluation. For example, a regression analysis may be performed to select the weighting coefficients that most reliably predict depression. Determination of optimal weighting coefficients may be performed by code executed by the controller of the implantable device or by, for example, an external programmer using a downloaded history of parameter values. In one embodiment, the manually actuated magnetic switch may be actuated by the patient when depression is felt to be present. The device controller and/or programmer may then be programmed to correlate the values of the different depression parameters with such manual actuations and thereby determine optimal weighting coefficients.

The mapping of parameter values to the depression index may be implemented as code executed by the device controller using an explicit mapping function (e.g., a weighed sum of parameter values) or as a table stored in memory that associates different sets of parameter values with a particular value of the depression index. A table may be derived from historical data in a similar manner to that described above for determining optimal weighting coefficients.

Device Response to Detection of Depression

In one embodiment, the device is equipped with drug delivery capability, where the device is configured to deliver a dose of medication when depression is detected in the manner described herein. A drug delivery system 500 is shown in FIG. 2 as interfaced to the device controller. Such a drug delivery system may be either an implantable system or an external drug delivery system such as described in U.S. Pat. No. 6,361,522, assigned to Cardiac Pacemakers, Inc. and hereby incorporated by reference.

In another embodiment, either in addition or instead of drug therapy, the device is configured to deliver neuromodulation therapy by electrically stimulating peripheral or central sites of the nervous system. The stimulation electrodes may be connected by a lead that is tunneled subcutaneously from the implanted device housing to a point of venous access or to a subcutaneous site. For example, the electrode could be implanted near the spine for stimulating an afferent nerve of a specific brain site or be disposed near a nerve such as the vagus. In order to directly stimulate and/or sense a site within the brain, a satellite unit may be implanted within the brain. For example, dysfunction of the prefrontal cortex may be associated with the mechanism of depression, and deep brain stimulation of the subgenual cingulate region or caudate has been reported to have a positive effect on patients with depression.

Figure 3:
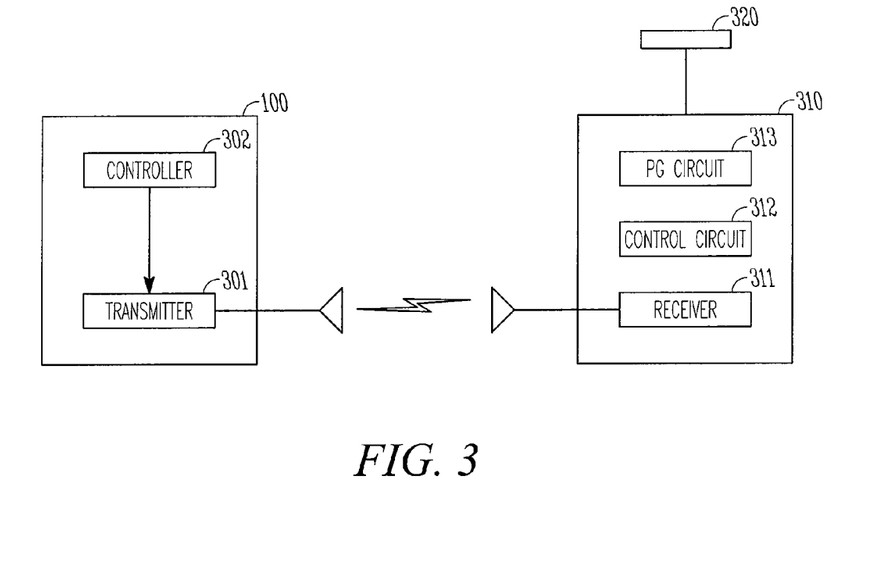
FIG. 3 illustrates a satellite unit for delivering neural stimulation or sensing.

FIG. 3 illustrates an embodiment of a neural stimulation and/or sensing channel where the leads of the neural stimulation electrodes are replaced by wireless links, and the electrodes for providing neural stimulation and/or sensing are incorporated into separately implantable satellite units. The wireless link may be, for example, a radio-frequency (RF) link or an acoustic link. The satellite unit 310 is an integrated assembly adapted for surgical implantation which includes a housing containing a battery and circuitry for outputting neural stimulation pulses to an external electrode which can clip around a target nerve (e.g., vagus, carotid sinus, or aortic nerve) be disposed near a site within the brain. The implantable device 100 includes a wireless telemetry transceiver, illustrated in this embodiment as a transceiver 301 (e.g., either an RF transceiver or an acoustic transducer) interfaced to the controller 302 for transmitting commands and/or receiving data, and the satellite unit 310 includes a wireless transceiver 311 interfaced to control circuitry 312 for receiving the commands and/or transmitting data. The control circuitry 312 translates the received commands and causes pulse generation circuitry 313 to output appropriate stimulation pulses to the external electrode 320.

Figure 4:
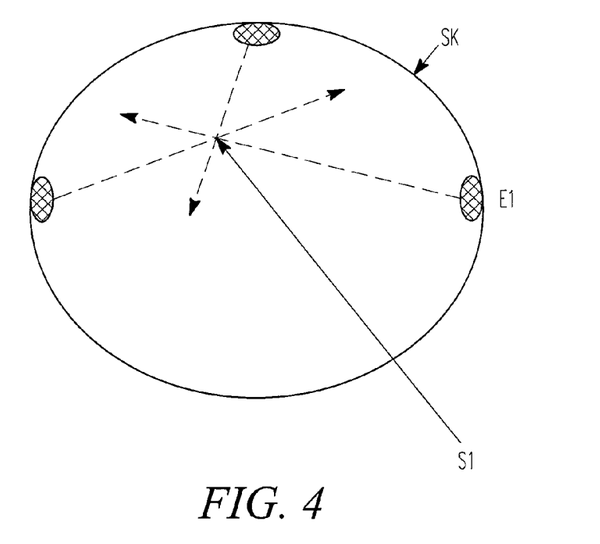
FIG. 4 shows an arrangement of electrodes for delivering stimulation to a site within the brain.

FIG. 4 illustrates another embodiment for providing neural stimulation to a site within the brain where one or more electrodes E1 are placed on or implanted into the skull SK. The electrodes E1 may be incorporated into satellite units or may be connected by leads to pulse generators within the device housing. By appropriate adjustment of the timing and amplitude of the stimulation pulses output by a plurality of the electrodes E1, neural stimulation is delivered to a vector determined point of stimulation S1 within the brain.

Figure 5:
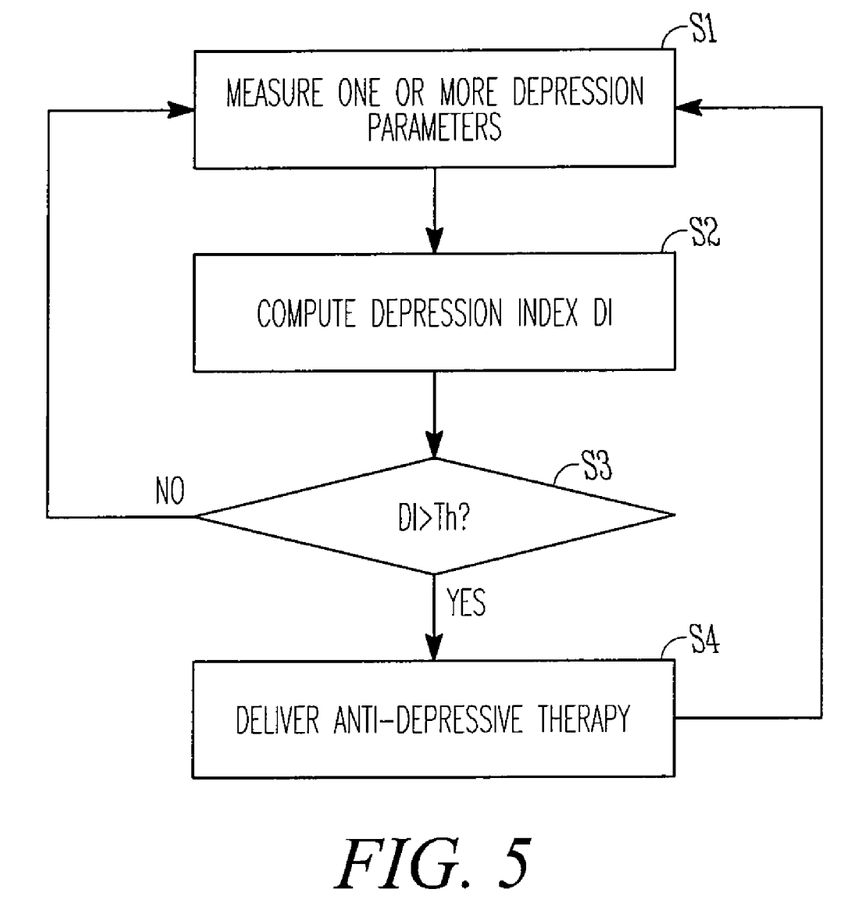
FIG. 5 shows an exemplary algorithm.

FIG. 5 shows an exemplary algorithm that can be implemented in the programming of the device controller to detect depression and deliver anti-depressive therapy in any of the embodiments described above. At step S1, the device collects one or more depression parameters. The depression index DI is computed at step S2, and compared with a specified threshold value Th at step S3. If the depression index exceeds the threshold value, anti-depressive therapy is delivered at step S4. After deliver of therapy or a negative comparison at step S3, the device continues to monitor depression parameters by returning to step S1.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. An implantable device, comprising:
    a sensing channel configured to collect values of one or more physiological variables in a patient;
    circuitry configured to derive one or more depression parameters that are correlated with depression in a patient from the one or more collected physiological variables;
    a sensing channel configured to generate an electrogram signal representing electrical activity in a cardiac chamber;
    circuitry configured to measure and collect time intervals between successive intrinsic beats, referred to as a BB interval, and storing the collected intervals as a discrete BB interval signal, filtering the BB interval signal into defined high and low frequency bands, and determine the signal power of the BB interval signal in each of the low and high frequency bands, referred to as LF and HF, respectively;
    circuitry configured to compute a heart rate variability parameter as an LF/HF ratio;
    circuitry configured to detect depression based upon the one or more depression parameters, wherein the one or more depression parameters includes the computed LF/HF ratio; and,
    wherein the circuitry configured to detect depression is further configured to cause delivery of anti-depressive therapy when depression is detected.

2. The device of claim 1 further comprising:
    a neural channel configured to deliver neural stimulation; and,
    wherein the circuitry configured to cause delivery of anti-depressive therapy is further configured to cause delivery of neural stimulation when depression is detected.

3. The device of claim 1 further comprising:
    a delivery device configured to deliver a dose of medication; and,
    wherein the circuitry configured to cause delivery of anti-depressive therapy is further configured to cause delivery of medication when depression is detected.

4. The device of claim 1 further comprising:
    one or more chemical sensing channels configured to generate a signal indicative of the concentration of a specific blood-borne marker associated with depression; and,
    wherein the one or more depression parameters includes one or more marker concentrations.

5. The device of claim 1 further comprising:
    a neural channel configured to measure neural activity at a particular site; and,
    wherein the one or more depression parameters includes the measured neural activity.

6. The device of claim 1 further comprising:
    a neural stimulation/sensing channel implemented as a separately implantable satellite unit;

means for allowing the circuitry configured to detect depression and the circuitry configured to cause delivery of anti-depressive therapy to communicate wirelessly with the satellite unit.

7. The device of claim 1 further comprising:
circuitry configured to map a plurality of depression parameters into a depression index; and,
wherein the circuitry configured to detect depression is further configured to compare the depression index with a specified threshold value.

8. The device of claim 7 wherein the depression index is a weighted sum or average of a number of different parameters associated with depression.

9. A method for operating an implantable device in order to treat depression, comprising:
generating an electrogram signal representing electrical activity in a cardiac chamber;
measuring and collecting time intervals between successive intrinsic heart beats, referred to as a BB interval, and storing the collected intervals as a discrete BB interval signal, filtering the BB interval signal into defined high and low frequency bands, and determining the signal power of the BB interval signal in each of the low and high frequency bands, referred to as LF and HF, respectively;
computing a heart rate variability parameter as an LF/HF ratio;
collecting values of one or more physiological variables via one or more sensing channels of an implantable device;
deriving one or more depression parameters that are correlated with depression in a patient from the one or more collected physiological variables;
detecting depression based upon the one or more depression parameters, wherein the one or more depression parameters includes the computed LF/HF ratio; and,
triggering delivery of anti-depressive therapy from the implantable device when depression is detected based upon the one or more depression parameters.

10. The method of claim 9 further comprising delivering of neural stimulation when depression is detected.

11. The method of claim 9 further comprising delivering medication from the implantable device when depression is detected.

12. The method of claim 9 further comprising:
generating a signal indicative of the concentration of a specific blood-borne marker associated with depression; and,
wherein the one or more depression parameters includes one or more marker concentrations.

13. The method of claim 9 further comprising:
measuring neural activity at a particular site; and,
wherein the one or more depression parameters includes the measured neural activity.

14. The method of claim 9 further comprising transmitting an alarm message over a network when depression is detected.

15. The method of claim 9 further comprising:
mapping a plurality of depression parameters into a depression index; and,
comparing the depression index with a specified threshold value in order to detect depression.

16. The method of claim 15 wherein the depression index is a weighted sum or average of a number of different parameters associated with depression.

* * * * *

UNITED STATES PATENT AND TRADEMARK OFFICE
CERTIFICATE OF CORRECTION

PATENT NO. : 7,606,622 B2  Page 1 of 1
APPLICATION NO. : 11/275682
DATED : October 20, 2009
INVENTOR(S) : Helen L. Reeve It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 594 days.

Signed and Sealed this

Twelfth Day of October, 2010

David J. Kappos
*Director of the United States Patent and Trademark Office*